United States Patent [19]

Schmidt

[11] 4,162,125

[45] Jul. 24, 1979

[54] PROCESS AND DEVICE FOR DETECTING INCLUSIONS IN CRYSTALS

[75] Inventor: Walter Schmidt, Schaffhausen, Switzerland

[73] Assignee: Swiss Aluminium Ltd., Chippis, Switzerland

[21] Appl. No.: 794,793

[22] Filed: May 9, 1977

[30] Foreign Application Priority Data

May 20, 1976 [CH] Switzerland ..................... 6321/76

[51] Int. Cl.² ............................................ G01N 21/32
[52] U.S. Cl. ..................................... 356/30; 356/239
[58] Field of Search .......................... 356/30, 237, 239

[56] References Cited

U.S. PATENT DOCUMENTS

| | | | |
|---|---|---|---|
| 3,586,444 | 6/1971 | Sproul et al. | 356/239 X |
| 3,867,032 | 2/1975 | Bruck | 356/30 |
| 4,021,217 | 5/1977 | Bondybey et al. | 356/239 X |

*Primary Examiner*—F. L. Evans
*Attorney, Agent, or Firm*—Robert H. Bachman

[57] ABSTRACT

Inclusion in crystals, in particular in single crystals of gallium-gadolinium garnet, are detected by passing a beam e.g. a laser beam into the crystal perpendicular to the long axis of the crystal. The crystal can be rotated and the light scattered by the inclusions in the crystal are recorded photographically at right angles to the illuminating beam which is made to scan the rod shaped crystal along its long axis.

17 Claims, 3 Drawing Figures

PROCESS AND DEVICE FOR DETECTING INCLUSIONS IN CRYSTALS

The invention concerns a process for detecting inclusions in crystals by means of a beam of energy which passes through the crystal, and concerns in particular the detection of inclusions in rod-shaped single crystals of gallium-gadolinium garnet. Furthermore, the invention is embodied in a device for carrying out this process.

In single crystals of gallium-gadolinium garnet (GGG) in particular, the crystal quality is judged not only by the incidence of dislocations but also by the presence of inclusions.

Inclusions which are known to occur are:
gas inclusions
inclusions of crucible material
precipitates of secondary phases.

Besides representing flaws in the crystal structure such inclusions can also be the source and cause of other crystal defects. Not only is it the number of inclusions in the crystal which is important, but also their distribution since they are often present only in small zones. By cutting out such zones the yield of good material can be increased.

The problem of rapid, accurate detection of all inclusions in the crystals has therefore become very important in the production of gallium-gadolinium garnet single crystals. For this purpose, normally both end faces of the rod-shaped crystals are polished and a powerful light shone down the central axis. Large inclusions can then be detected by the light they scatter; because of optical distortion, however, their exact position is difficult to determine. Small inclusions have to be detected microscopically at extremely large distances from the objective lens i.e. deep inside the crystal which is often up to 20 cm in length. Besides the awkwardness, this method also involves the well known difficulty of polishing the end faces of the crystal.

With these facts in mind the inventor set out to develop a process and device of the kind described at the beginning, by means of which process the difficulties encountered in detecting inclusions in crystals are avoided.

To overcome the problems involved the inventor had the idea of examining the crystals in the direction transverse to the direction of the beam of energy passing through the crystal, if necessary rotating the crystal about its long axis. In accordance with the invention the crystal should be photographed in the direction transverse to the direction of the beam and, in accordance with another feature of the invention, the beam should be moved at least in the direction transverse to the direction of observation.

It has been found particularly favorable to direct the beam into the crystal in a direction radial to the long axis of the crystal and at the same time to move the beam in a direction approximately parallel to that long axis.

The crystal is again observed preferrably in the radial direction which, apart from separating the inclusions in the field of view, also gives the advantage that the end faces no longer need to be polished but instead the cylindrical surface of the crystal is polished which is easier to perform.

In accordance with another feature of the invention the crystal is placed on a device which makes the crystal rotate and on which a beam of energy, approximately parallel to the long axis of the crystal and entering the crystal, for example a laser beam, moves perpendicular to its long axis. This movement of the laser beam is usefully coordinated with the speed of rotation of the crystal.

It is within the scope of the invention that at least two shafts which can be rotated or similar facilities are provided, and the crystal is placed on these. Instead of this, each shaft can be stationary and can be fitted with parts which rotate.

On that rotation device a reflector moves approximately parallel to the long axis of the crystal and deflects the laser beam into the crystal in the required direction, for example in a radial direction, to illuminate the crystal. The position of the beam emitting source determines whether this reflector is positioned approximately diagonally to that long axis or at another angle.

A mirror which is mounted on a base that can be moved by a screw mechanism has been found to be a particularly good reflector; a mask with an aperture which cuts the beam at the sides can be provided in line after this reflector.

A laser device is preferred as the energy source here. The laser beam passing through the crystal is of high intensity and, because of its extreme coherency, the scattering which occurs at inhomogeneities in the crystal is especially strong. Since the laser beam has a diameter of only 1–2 mm, it illuminates only a small volume of the crystal at any one moment of time.

In order to examine a larger volume therefore, the crystal is made to rotate and, at the same time, the laser beam is moved slowly along the length of the crystal.

If, as mentioned above, the whole device is placed in a photographic unit and the laser beam made to scan the crystal once, then a photographic record of the crystal is obtained. Perfect regions do not scatter the beam and therefore are not recorded; scattering centers such as inclusions on the other hand are recorded photographically as bright spots.

The photographic record thus obtained shows first of all the number of inclusions in the crystal and also the distribution of these along the axis of the crystal. Such a photograph then serves as a reference for further processing of the crystal and also as a record of the crystal quality. Furthermore, it is now possible for the first time to cut out individual defective parts from the crystal without affecting a large part of the crystal which is free of defects.

Further advantages, features and details of the invention will now be explained by means of the following description of a preferred embodiment of the invention and with the aid of the drawings viz., FIG. 1 A schematic perspective view of a device in accordance with the invention.

FIG. 2 A photographic image of a crystal with inclusions concentrated at one end.

FIG. 3 A photographic image of another, almost inclusion-free crystal.

A base 1 is divided into two parts 4,5 and has two walls 2,3 across its breadth. In the larger part 4 (at the front in FIG. 1) there are two shafts 6 carrying pairs of rings 7 on which the crystal K rests. One of the rings, 7s in FIG. 1, is for example stepped along its length in order to be able to provide proper support for crystals K of different diameters d.

A motor device M turns either both shafts 6 completely or only the support rings 7 in the direction of the arrow Z, and thus rotates a single crystal K of length P, for example 11 cm, resting on the support rings 7. The crystal K thus rotates continuously around its long axis A in the direction of the arrow q.

A block 9 is moved parallel to the long axis A of the crystal by means of the threaded shaft 8 and mounted on the block 9, there is a mirror 10, set diagonal to the direction of movement of the block 9. The speed at which the block 9 moves along in the direction x can be varied and, by means of a device which is not shown here, the said rate of movement can be regulated as a function of the speed of rotation of the crystal K.

A laser beam 11 is emitted from a laser device 11 and directed parallel to the long axis A and, in the example chosen here, is deflected through 90° by the mirror 10. This beam then passes radially through the crystal K.

In order to cut off the outer region of the beam and thus entrance contrast, a mask 12 with a slit-shaped aperture is provided in the path of the beam between the mirror 10 and the crystal K.

The whole device 1 is situated below a camera F which is used to photograph the rotating, illuminated crystal K in the direction y, as the laser beam is moved along the long axis A. The exposure process and movement of the block 9 are limited by a switch which is not shown in the drawing.

Figure 1:
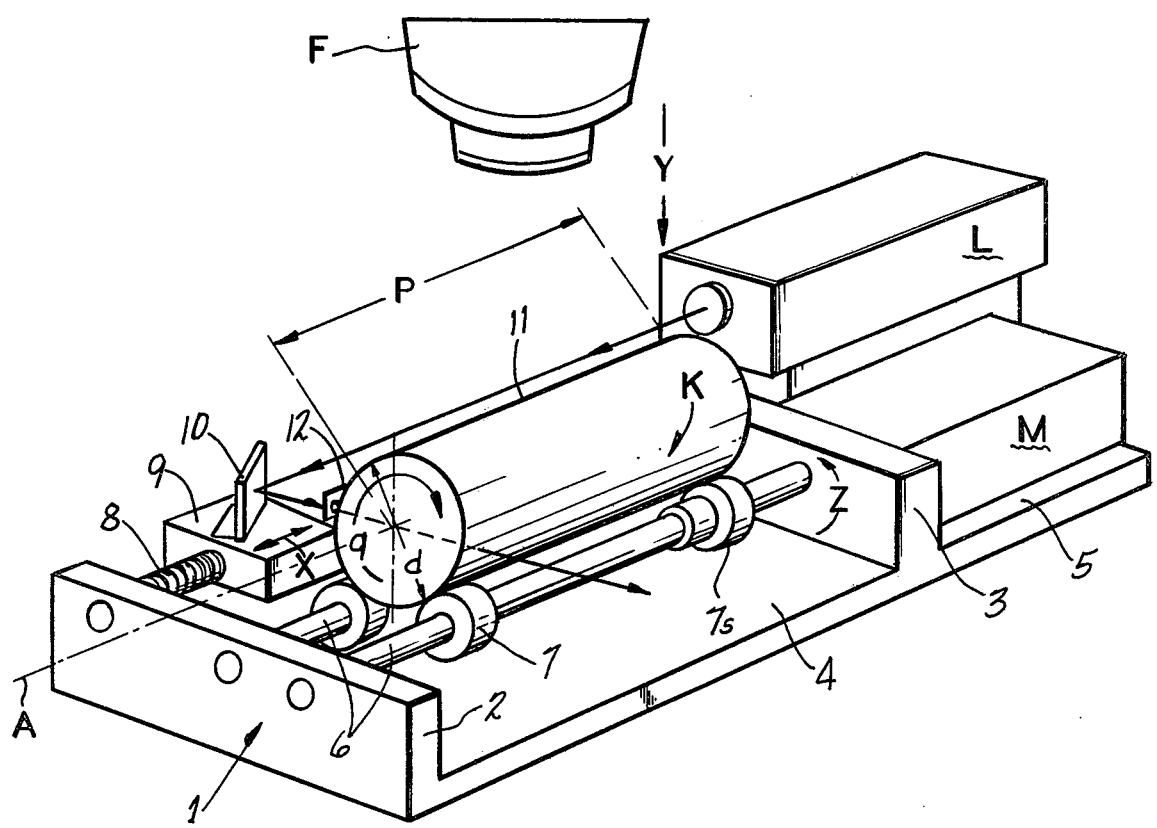
Figure 2:
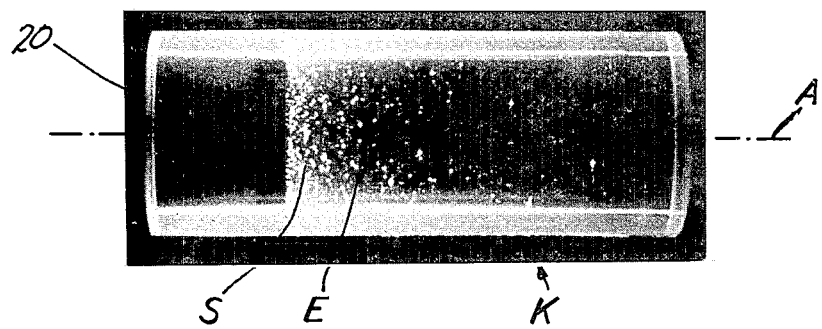
FIG. 2 shows a crystal K with scattering centers S due to inclusions E near one of the end faces 20; these inclusions appear as bright spots.
Figure 3:
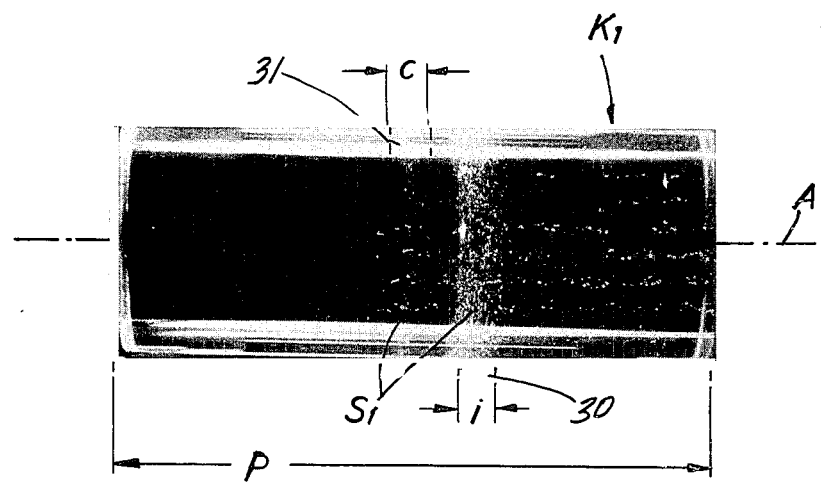
FIG. 3 shows another crystal K, in which the areas free of defect can be recognized by the absence of bright spots; here scattering centers S can be seen only in the region of two narrow bands 30,31 of width i and c respectively.

What is claimed is:

1. In a process for detecting inclusions in a rod-shaped single crystal of gallium-gadolinium garnet having a long axis, the steps comprising:
    placing said crystal in air;
    passing a concentrated beam of energy of high intensity through said crystal in a direction substantially perpendicular to the long axis of the crystal; and
    observing said crystal in direct face-to-face relationship in a direction approximately perpendicular to the direction of the beam which passes through said crystal, whereby inclusions in said crystal are detected by scattering said beam.

2. A process according to claim 1 including the step of photographing said crystal in a direction approximately perpendicular to the direction of said beam which is passed through said crystal.

3. A process according to claim 1 including the step of moving said beam in a direction approximately perpendicular to the direction of said observation.

4. A process according to claim 1 wherein said beam of energy is passed through said crystal in a direction approximately radial to the long axis of said crystal and at the same time said beam is moved approximately parallel to said long axis.

5. A process according to claim 1 including the step of rotating said crystal about its long axis while said crystal is exposed to said beam of energy.

6. A process according to claim 1 wherein said beam is a laser beam and including the step of moving at least one reflector approximately parallel to the long axis of said crystal so that said laser is deflected to said long axis.

7. A process according to claim 5 wherein said beam is a laser beam and including the steps of moving said laser beam in a direction approximately perpendicular to the direction of observation and coordinating said movement of said laser beam with the speed of rotation of said crystal.

8. A device for detecting inclusions in a rod-shaped single crystal of gallium-gadolinium garnet having a long axis which comprises:
    means for supporting said crystal in air;
    means for projecting a concentrated beam of energy of high intensity so that said beam of energy travels in a direction substantially perpendicular to said long axis of said crystal; and
    means for observing said crystal approximately perpendicular to the direction in which said beam of energy is traveling when it enters said crystal, whereby inclusions in said crystal are detected by scattering said beams and are observed in direct face-to-face relationship.

9. A device according to claim 8 including means for rotating said crystal about its long axis, means for moving said beam of energy along in a direction approximately parallel to the long axis of said crystal, and means for projecting said beam of energy so that said beam of energy enters said crystal approximately in a radial direction to said long axis.

10. A device according to claim 8 including at least two rotating supports for said crystal.

11. A device according to claim 10 wherein said rotating supports comprise sleeves having different diameters.

12. A device according to claim 8 including a reflector mounted so as to be movable in a direction approximately parallel to the long axis of said crystal and operable so as to deflect said beam of energy into a direction approximately radial to said long axis.

13. A device according to claim 12 wherein said reflector comprises a mirror, support means for said mirror, and means for moving said mirror and said support means.

14. A device according to claim 12 including masking means mounted between said reflector and said crystal defining an aperture which limits the width of said beam.

15. A device according to claim 8 wherein a projecting means projects said beam substantially parallel to the long axis of said crystal, said device further including a mirror positioned at an angle with respect to the long axis of said crystal, said mirror being operable to deflect a beam into said long axis of said crystal.

16. A device according to claim 8 wherein said projecting means is a laser beam projecting means which provides a laser beam for illuminating said crystal.

17. A device according to claim 8 including a photographic device mounted so as to photograph said crystal at least in the region in which said crystal is illuminated by said beam of energy.

* * * * *